US007632389B2

(12) United States Patent
Wen et al.

(10) Patent No.: US 7,632,389 B2
(45) Date of Patent: Dec. 15, 2009

(54) OPEN TUBE SUITABLE FOR SEPARATION PURPOSES COMPRISING COVALENTLY BONDED ZWITTERIONIC BETAINE GROUPS

(75) Inventors: Jiang Wen, Umeå (SE); Knut Irgum, Bullmark (SE)

(73) Assignee: Merck Patent GmbH, Darmstadt (DE)

( * ) Notice: Subject to any disclaimer, the term of this patent is extended or adjusted under 35 U.S.C. 154(b) by 973 days.

(21) Appl. No.: 10/819,215

(22) Filed: Apr. 7, 2004

(65) Prior Publication Data

US 2004/0256232 A1 Dec. 23, 2004

Related U.S. Application Data

(60) Provisional application No. 60/461,125, filed on Apr. 9, 2003.

(51) Int. Cl.
*G01N 27/453* (2006.01)
*G01N 30/02* (2006.01)
*F16L 9/10* (2006.01)

(52) U.S. Cl. .................. 204/601; 422/70; 428/34.4

(58) Field of Classification Search ......... 204/601–605, 204/451–455; 422/70; 210/656
See application file for complete search history.

(56) References Cited

U.S. PATENT DOCUMENTS 5,415,747 A   5/1995   Holloway

OTHER PUBLICATIONS

Jiang et al. "Control of Electroosmotic Flow and Wall Interactions in Capillary Electrophoresis Capillaries by Photografted Zwitterionic Polymer Surface Layers," Anal. Chem. 2003, 75, 2768-2774, Jun. 1, 2003.*
Dean, J. A., Ed. *Lange's Handbook of Chemistry*, 13th ed.; McGraw-Hill: New York, 1985: pp. 6-34.
Baryla, N. E.; Lucy C. A. *J. Chromatogr.*, A 2002, 956, 271-277.
Cunliffe, J. M.; Baryla, N.; Lucy, C. A. *Anal. Chem.* 2002, 74, 776-783.
Li, Y. M.; Liao, J. L.; Nakazato, K.; Mohammed, Terenius, L.; Hjerten, S. *J. Anal. Biochem.* 1994, 223, 153-158.
Atamna, I. Z.; Issaq, H. J.; Muschik, G. M.; Janini, G. M. *J. Chromatogr.* 1991, 588, 315-320.
Jones, W. R.; Jandik, P. *J. Chromatogr.* 1991, 546, 445-458.
Towns, J. K.; Regnier, F. E. *Anal. Chem.* 1991, 63, 1126-1132.
http://www.up.univ-mrs.fr/_wabim/.
Jiang, et al., UMEA Universite, "Control of Electroendoosmotic Flow and Wall Interactions in CE Capillaries by Photografted Switterionic Surface Layers", HPCE 2002, Sweden, Apr. 17, 2002, 1 page.
Hu, S.; Dovichi, N. J. Anal. Chem. 2002, 74, 2833-2850.
Rodrigueza, I.; Li, S. F. Y. *Anal. Chim. Acta* 1999, 383, 1-26.

(Continued)

*Primary Examiner*—Alex Noguerola
(74) *Attorney, Agent, or Firm*—Millen, White, Zelano & Branigan, P.C.

(57) ABSTRACT

A novel open tube with a zwitterionic betaine polymer layer can be prepared by initiated grafting polymerization. This open tube can be used for separating inorganic anions, peptides and proteins. A capillary electrophoresis method and a capillary chromatography method use the novel open tube. There are methods for manufacturing the novel open tube.

5 Claims, 10 Drawing Sheets

OTHER PUBLICATIONS

Righetti, P. G.; Gelfi, C.; Verzola, B.; Castelletti, L. *Electrophoresis* 2001, 22, 603-611.
Liu, C. Y. *Electrophoresis* 2001, 22, 612-628.
Horvath, J.; Dolnik, V. *Electrophoresis* 2001, 22, 644-655.
Chen, S. H.; Pietryk, D. J. *Anal. Chem.* 1993, 65, 2770-2775.
Pietryk, D. J.; Chen, S.; Chanthawat, B. *J. Chromatogr., A* 1997, 775, 327-338.
Minnoor, E.; Liu, Y.; Pietryk, D. J. *J. Chromatogr., A* 2000, 884, 297-309.
Hu, W.; Haddad, P. R. *Trends Anal. Chem.* 1998, 17, 73-79.
Nesterenko, P. N.; Haddad, P. R. *Anal. Sci.* 2000, 16, 565-574.
Jiang, W.; Irgum, K. *Anal. Chem.* 1999, 71, 333-344.
Jiang, W.; Irgum, K. *Anal. Chem.* 2001, 73, 1993-2003.
Jiang, W.; Irgum, K. *Anal. Chem.* 2002, 74, 4682-4687.
Viklund, C.; Irgum, K. *Macromolecules* 2000, 33, 2539-2544.
Viklund, C.; Sjogren, A.; Irgum, K. *Anal. Chem.* 2001, 73, 444-452.
Swedberg, S. A. *J. Chromatogr.* 1990, 503, 449-452.
Strege, M. A.; Lagu, A. L. *J. Liq. Chromatogr.* 1993, 16, 51-68.
Greve, K. F.; Nashabeh, W.; Karger, B. L. *J. Chromatogr., A* 1994, 680, 15-24.
Gong, B. Y.; Ho, J. W. *Electrophoresis* 1997, 18, 732-735.
Yeung, K. K.-C.; Lucy, C. A. *Anal. Chem.* 1997, 69, 3435-3441.
Baryla, N. E.; Lucy C. A. *Anal. Chem.* 2000, 72, 2280-2284.
Woodland, M. A.; Lucy, C. A. *Analyst* 2001, 126, 28-32.
Castelletti, L.; Verzola, B.; Gelfi, C.; Stoyanov, A., Righetti, P. G. *J. Chromatogr., A* 2000, 894, 281-289.
Yokoyama, T.; Macka, M.; Haddad, P. R. *Fresenius J. Anal. Chem.* 2001, 371, 502-506.
Mori, M.; Hu, W. Z..; Haddad, P. R.; Fritz, J. S.; Tanaka, K.; Tsue, H.; Tanaka, S. *Anal. Bioanal. Chem.* 2002, 372, 181-186.

\* cited by examiner

Scheme 1

Scheme 2

OPEN TUBE SUITABLE FOR SEPARATION PURPOSES COMPRISING COVALENTLY BONDED ZWITTERIONIC BETAINE GROUPS

This application claims benefit to provisional application 60/461,125 filed on Apr. 9, 2003.

FIELD OF THE INVENTION

The present invention relates to a novel open tube that can be used in separation techniques employing open tubes such as high performance capillary electrophoresis (HPCE) and capillary chromatography. More particularly, the present invention relates to an open tube comprising covalently bonded zwitterionic betaine groups as well as separation methods using such an open tube.

BACKGROUND OF THE INVENTION

Separation techniques using open tubes, such as Capillary Chromatography and Capillary Electrophoresis (CE) have become universal and important tools for separating inorganic anions, peptides and proteins. This is because of the high separation efficiency, the good resolution, the faster separation, and the lower consumption of samples and solutions that can generally be achieved compared to liquid chromatographic techniques.

Although CE has been known for several decades, new developments and applications continue to be forthcoming with approximately 3,000 papers presently published annually in the field. (Hu et al, Anal. Chem. 2002, 74, 2833-2850.) One area of research within the field of CE is the study of wall chemistry. This research focuses on ways to prevent wall adsorption and suppress EOF, which in turn improve the separation efficiency and resolution of different analytes. For example, inorganic anions are very difficult to separate with native silica capillaries unless very high salt concentrations and very low pH are used to suppress the EOF, because the EOF direction is opposite to the electrophoretic movement of anions. For anions with high electrophoretic mobility, the separation time becomes much longer, whereas anions having low electrophoretic mobility may in extreme cases be transported out of the capillary by the EOF at the injection end of the capillary. The negative charge that the native silica capillary surface expresses over a wide pH range is also problematic in the separation of positive charge molecules such as basic proteins because of electrostatic interaction. Therefore, the EOF must be suppressed or even reversed by shielding or altering the surface charge, in order to obtain fast separations and improve separation efficiency. Many approaches, including adjusting the concentration or pH of the buffer, adding small cationic-type solutes or various detergents or polymers, and attaching a static covalently-bonded polymer layer on the lumen surface have been developed to fulfill this task. (Rodrigueza et al, Anal. Chem. Acta 1999, 383, 1-26; Righetti et al, Electrophoresis 2001, 22, 603-611; Liu, Electrophoresis 2001, 22, 612-628; Horvath et al, Electrophoresis 2001, 22, 644-655; Chen et al, Anal. Chem. 1993, 65, 2770-2775; Pietryk et al, J. Chromatogr., A 1997, 775, 327-338; Minnoor et al, J. Chromatogr., A 2000, 884, 297-309.) All these modifications have shown varying degrees of improvement on the separation of different samples.

Although zwitterionic separation materials, prepared either by dynamically coating or covalently bonding zwitterionic functionalities, have been used for long time in liquid chromatography (Hu et al, P.R. Trends Anal. Chem. 1998, 17, 73-79; Nesterenko et al, Anal. Sci. 2000, 16, 565-574; Jiang et al, Anal. Chem. 1999, 71, 333-344; Anal. Chem. 2001, 73, 1993-2003; Anal. Chem. 2002, 74, 4682-4687; Viklund et al, Macromolecules 2000, 33, 2539-2544; Viklund et al, Anal. Chem. 2001, 73, 444-452.), there are only limited studies involving modified capillaries in CE with zwitterionic functionality. Most of these studies are focused on suppressing the EOF and preventing wall adsorption by zwitterionic surfactants. The different approaches have demonstrated a potential for improving the separation efficiency of inorganic and organic anions or cations, peptides, and proteins. (U.S. Pat. No. 5,415,747; Swedberg, J. Chromatogr. 1990, 503, 449-452; Strege et al, J. Liq. Chromatogr. 1993, 16, 51-68; Greve et al, J. Chromatogr., A 1994, 680, 15-24; Gong et al, Electrophoresis 1997, 18, 732-735; Yeung et al, Anal. Chem. 1997, 69, 3435-3441; Baryla et al, Anal. Chem. 2000, 72, 2280-2284; Woodland et al, Analyst 2001, 126, 28-32; Castelletti et al, J. Chromatogr., A 2000, 894, 281-289; Yokoyama et al, Anal. Chem. 2001, 371, 502-506; Mori et al, Anal. Bioanal. Chem., 2002, 372, 181-186.) Nonetheless, the dynamic coating procedure requires that the zwitterionic surfactant be added to the separation solution in order to get a reproducible surface, a prerequisite for good reproducibility in the separation.

The addition of zwitterionic surfactant results a more complicated separation matrix; their presence causes interference in certain detection schemes such as mass spectrometry (Baryla et al, J. Chromatogr., A 2002, 956, 271-277; Cunliffe et al, Anal. Chem. 2002, 74, 776-783.) and also adds to the complexity of samples that are fraction collected for subsequent use or analysis. Although Cunliffe et al. have tried to use the zwitterionic surfactant with double carbon chains to obtain semi-permanent layers on the capillary surface, the stability of the layer is still an important issue. This is because the mixture containing the zwitterionic surfactant and other chemicals has to be used to flush the capillary between runs of separating proteins, which results longer experiment time. (Cunliffe et al, Anal. Chem. 2002, 74, 776-783.) Accordingly, there is a need in the art for synthesis of capillaries with covalently-bonded zwitterionic functionalities both in order to investigate basic separation properties and for comparison with capillaries dynamically coated with zwitterionic surfactants. U.S. Pat. No. 5,415,747 suggests that a zwitterionic species may be bonded to capillaries though a direct silicon-carbon linkage. However, no results are provided regarding a capillary which comprises covalently bonded zwitterionic groups. Consequently, there is a need for further improvements in the field of capillary electrophoresis and capillary chromatography.

SUMMARY OF THE INVENTION

Accordingly, the present invention provides a novel open tube, in particular a capillary, with a zwitterionic betaine polymer layer prepared by grafting polymerization. This open tube can be used for separating inorganic anions, peptides and proteins. The invention also provides a capillary electrophoresis method and a capillary chromatography method using the novel open tube as well as a method for manufacturing the open tube.

DETAILED DESCRIPTION OF THE INVENTION

Figure 1:
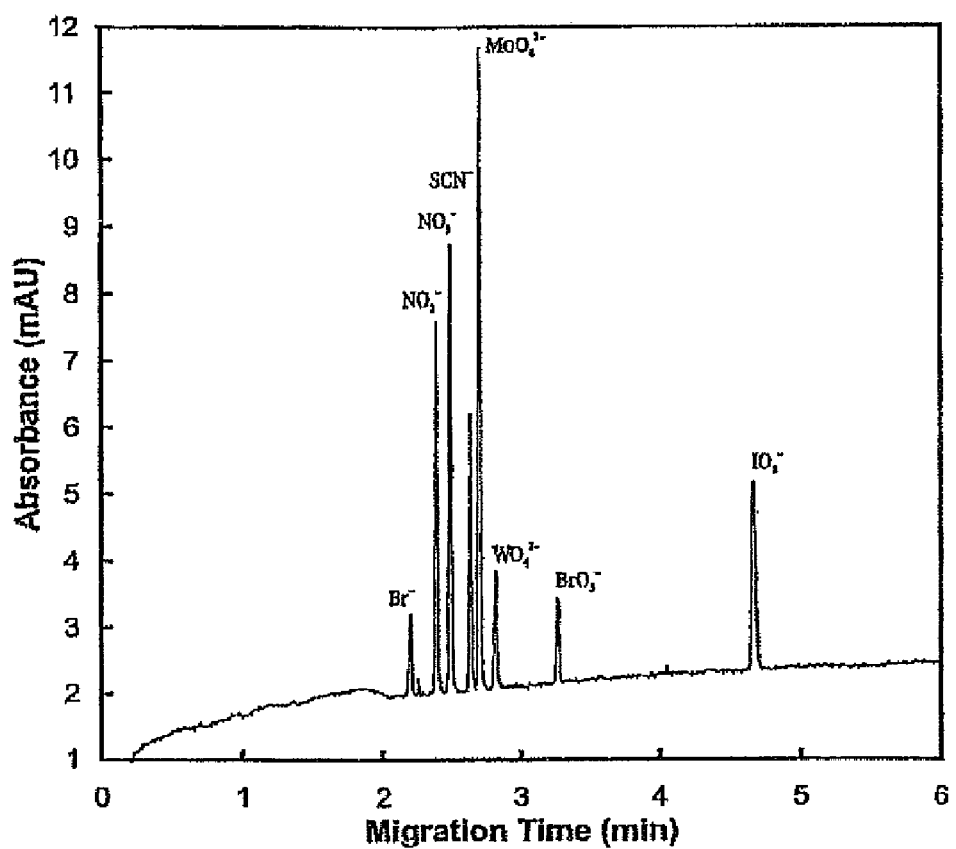
FIG. 1 discloses an electropherogram for the separation of eight inorganic anions where detection=214 nm, applied voltage=−25 kV, capillary=50 μm i.d. by 50/57 cm, separation buffer=35 mM pH 7 phosphate buffer.

Before the invention is described in detail, it is to be understood that the terminology used herein is for the purpose of describing particular embodiments only and is not intended to be limiting.

In this specification and in the claims, which follow, reference will be made to a number of terms, which shall be defined to have the following meanings:

The term "zwitterionic group" is used in its conventional sense to mean a single group containing both a cationic part and an anionic part at a particular pH range.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain 1 to 12 carbon atoms. The term "lower alkyl" means an alkyl group of one to six carbon atoms, e.g., methyl, ethyl, n-propyl, isopropyl, n-butyl, isobutyl, t-butyl, and the like.

The term "alkylene" as used herein refers to a difunctional saturated branched or unbranched hydrocarbon chain containing from 1 to 24 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like. The term "lower alkylene" refers to an alkylene group of 1 to 6 carbon atoms, e.g., methylene, ethylene, propylene, and the like.

The term "arylene" refers to a difunctional aromatic moiety; "monocyclic arylene" refers to a phenylene group. These groups may be substituted with up to four ring substituents which are generally, although not necessarily, selected from the group consisting of halogen, alkyl (typically lower alkyl), alkoxy (typically lower alkoxy), acyl (typically lower acyl), and nitro. Other aromatic substituents are possible as well, providing that they are not ionically charged at the pH of the electrophoretic separation.

The term "alkarylene" refers to a difunctional moiety containing an arylene group and an alkylene group. The term "lower alkarylene" refers to an alkarylene group containing less than 12 carbon atoms.

The term "oxyalkylene" refers to an alkylene linkage containing 1 to 24 carbon atoms and 1 to 3 ether linkages. Preferred oxyalkylene groups are alkylene linkages containing a single ether linkage at a terminus, i.e., —(CH$_2$)$_n$—O—. The term "lower oxyalkylene" intends an oxyalkylene group containing 1 to 6 carbon atoms and a single, preferably terminal, ether linkage.

"Halo" or "halogen" refers to fluoro, chloro, bromo or iodo, and usually relates to halo substitution for a hydrogen atom in an organic compound. Of the halos, chloro and fluoro are generally preferred.

A "siloxane" as used herein is a compound, which contains one or more silicon-oxygen bonds. The term "siloxyl" refers to a siloxane radical. The term "silyl" unless otherwise specified means a linkage which contains a silicon atom.

According to the present invention, a zwitterionic coating is incorporated into an electrophoresis apparatus by covalently bonding a zwitterionic species to the interior surface of the capillary tube. The zwitterionic species may be bonded through a siloxane linkage or it may be bonded through a silicon-carbon bond. It may be bonded directly, through one or more linking groups, or through a polymeric species.

The zwitterionic species used in conjunction with the invention are betaines containing a negatively charged group and a quaternary ammonium group. Examples of such betaines are sulfobetaines containing both an SO$_3$—moiety and a quaternary ammonium group. The zwitterionic species according to this embodiment may accordingly be represented as:

*L$^1$-N$^+$R$_2$-L$^2$-SO$_3^-$   (1)

where L$^1$ and L$^2$ are optional linking groups, and * represents the point of attachment of the zwitterionic species to the silica surface. L$^1$ and L$^2$ are generally selected from the group consisting of alkylene, oxyalkylene, alkylene containing an ester linkage (i.e., (CH$_2$)$_a$—COO—(CH$_2$)$_b$ where a and b are integers in the range of 0 to 24 inclusive, with the proviso that both are not 0 simultaneously), alkarylene, silyl, siloxyl, and combinations thereof. In a preferred embodiment, L$^1$ is selected from the group consisting of lower alkylene, lower oxyalkylene —O—(CH$_2$)$_c$-where c is an integer in the range of 1 to 6 inclusive, lower alkylene with a single ester linkage (i.e., —$(CH_2)_a$—COO—$(CH_2)_b$ where a and b are integers in the range of 1 to 6 inclusive, with the proviso that the sum of a and b is 6 or less), siloxyl-O—Si—, and combinations thereof.

Examples of betaines that can be used in accordance with the present invention are betaine methacrylic acid amidopropyl-dimethyl ammonium betaine and the sulfobetaines N,N-dimethyl-N-methacryloxyethyl-N-(3-sulfopropyl)-ammonium betaine, pyidinium, 2-ethenyl-1-(3-sulfopropyl)-hydroxide, inner salt, and trimethoxysilylpropyl-N-(3-sulfopropyl)-ammonium betaine.

If the zwitterionic species is covalently attached to the capillary tube surface through a siloxane bond, the siloxane linkage will typically be of the formula $Si^1$—O—$Si(OR^1)_2$—, where $Si^1$ represents a surface silicon atom contained in the capillary wall, $R^1$ is a lower alkyl, such that —O—$Si(OR^1)_2$— is a part of $L^1$. This type of surface modification may be readily effected by reaction of the surface silanol groups $Si^1$—OH with a monomeric siloxane having the formula R—$Si(OR^1)_3$ where R is or contains the zwitterionic species and $R^1$ is as defined above. Such reactions are well known in the art and are described, for example, by Halasz and Sebastian, Angew Chem. (Int. Ed.)8:453 (1969), Duel et al., Helv. Chim. Actal 19:1160 (1959), and Hunter et al., Indust. and Engin. Chem. 39:1389 (1947), as well as in U.S. Pat. No. 3,965,179 to Sebastian.

Alternatively, the zwitterionic species may be covalently bound to the silica surface through a silicon-carbon linkage. Such linkages are stable to extremes of pH, and may be readily prepared using methods known in the art, such as described in U.S. Pat. No. 4,904,632 to Pesek et al. Briefly, the method involves halogenation of the silica surface using, typically, a Lewis base halogenating reagent such as thionyl chloride, thionyl bromide or phosgene, in an anhydrous, aprotic solvent such as toluene. A vacuum is applied to the capillary, such that the reactants are drawn therein. The reaction is allowed to proceed until completion, typically involving a reaction temperature of approximately 50° C. or higher and a reaction time of about 16-18 hours, at which point it may be presumed that the majority of the surface silanol groups have been converted to Si-Z groups, where Z is a halogen atom. This step is then followed by alkylation using either a Grignard reagent Zw-MgBr or ZwLi where Zw represents the zwitterionic species, i.e., either of those illustrated in Formulae (1) and (2). This produces a covalently-bound zwitterionic species wherein the linkage to the silica surface is through a direct Si—C bond. A similar reaction is described by K. A. Cobb et al., in Anal. Chem. 62:2478-2483 (1990).

The present invention also relates to a method of manufacturing a capillary having an interior surface provided with covalently-bounded zwitterionic betaine groups. The starting material of the method is a fused silica capillary tube which may optionally be UV-transparent. Silanol groups on the inside of the capillary tube are reacted with an anchoring methacrylic trimethoxysilane derivative. In one embodiment a methacrylic trimethylsilane derivative is 3-methacryloyloxypropyl-trimethoxysilane. Then, a methacrylic zwitterionic betaine monomer is added to the inside of the capillary tube together with a photoinitiator. Preferably, the methacrylic zwitterionic sulfobetaine monomer is N,N-dimethyl-N-methacryloxyethyl-N-(3-sulfopropyl) ammonium betaine. Preferably, the photoinitiator is benzoin methyl ether. Subsequently, photopolymerization is induced by exposing the capillary tube to UV light, preferably at a wavelength of at most 365 nm.

However, it is also possible to synthesize the zwitterionic capillaries by thermo-initiated graft polymerization. Silanol groups on the inside of the capillary tube are reacted with an anchoring methacrylic trimethoxysilane derivative in the same manner as outlined above. Then, a methacrylic zwitterionic betaine monomer is added to the inside of the capillary tube together with a thermal initiator.

The betaine methacrylic acid amidopropyl-dimethyl ammonium betaine, the sulfobetaines N,N-dimethyl-N-methacryloxyethyl-N-(3-sulfopropyl)-ammonium betaine, pyidinium, 2-ethenyl-1-(3-sulfopropyl)-hydroxide, inner salt, and trimethoxysilylpropyl-N-(3-sulfopropyl)-ammonium betaine can all of course be used in the above-mentioned methods for producing zwitterionic capillaries.

The present invention also relates to methods for separating component elements contained within a sample solution using capillary electrophoresis. The present method involves using an electrophoresis apparatus having a capillary tube, a means for introducing the sample solution into the capillary tube, a means for applying an electric field across the length of the capillary tube, and a component detecting means. The capillary tube is comprised of fused silica having a zwitterionic sulfobetaine coating on its interior surface. The zwitterionic sulfobetaine coating comprises a zwitterionic sulfobetaine species covalently bound to the interior surface through a covalent linkage. An electric field is applied across the length of the capillary tube such that the sample solution moves through the tube and the component elements therein are spatially separated. Finally, the presence of the individual component elements is detected.

As will be appreciated by those working in the field of capillary electrophoresis, the above-described method may be used in conjunction with a wide variety of capillary electrophoresis systems. An example of such a system can be found in U.S. Pat. No. 5,180,475.

Where a source is not indicated, equipment and reagents are commercially available and appropriate sources are known to a skilled worker. For the purposes of experimentation, a Beckman P/ACE 2100 capillary electrophoresis system (Beckman Coulter, Palo Alto, Calif.) which comprised an UV absorbance detector and Gold software data acquisition system were used. Untreated fused silica capillaries (375 μm o.d. by 50 μm i.d.) with UV-transparent perfluorinated polymer coatings from Polymicro Technologies (Phoenix, Ariz.) were used. Measurements were performed by UV spectrophotometry detection at 214 nm. The cooling system of the Beckman instrument was modified from liquid cooling to air cooling, to prevent the coolant from damaging the perfluorinated polymer coating and making the capillaries brittle.

The zwitterionic monomer, N,N-dimethyl-N-methacryloxyethyl-N-(3-sulfopropyl) ammonium betaine (SPE), was a gift from Raschig Chemie (Ludwigshafen, Germany). Benzoin methyl ether (BME, 98%), 3-methacryloyloxypropyl-trimethoxysilane (MAPTMS, 98%), and magnesium perchlorate (p.a.) were obtained from Aldrich (Steinheim, Germany or Milwaukee, Wis.). The salts $Na_2MoO_4.2H_2O$, $NaNO_2$, $NaNO_3$, $MgCl_2$, sodium dihydrogen phosphate and disodium hydrogen phosphate were of p.a. purity and from Merck (Darmstadt, Germany), as was the benzyl alcohol and the ammonium acetate. NaCl, $NaClO_4$, NaSCN were from Fluka (Buchs, Switzerland), whereas $NaIO_3$ was obtained from Mallinckrodt Chemicals Works (St. Louis, Mo.). $Na_2WO_4.2H_2O$ (p.a.) and $KBrO_3$ (p.a.) were from BDH Chemicals Ltd. (Poole, England), and KBr was from Riedel-de Haën (Seelze, Germany). All inorganic salt and buffer solutions were prepared by directly dissolving the appropriate salts in water, which was deionized by a Milli-Q (Millipore, Bedford, Mass.) water purification system. The buffer solutions were prepared from 100 mM stock solutions by varying the different ratios and degassed with helium for 10 minutes before experimentation.

The following peptides and proteins, used as test solutes, were purchased from Sigma (St. Louis, Mo.): angiotensin II (A9525), bradykinin (B3259), Gly-His-Lys (G1887), neurotensin (N6383), Gly-Arg-Gly-Asp (G3892), lysozyme from chicken egg white (L6876), cytochrome C from horse heart (C7752), ribonuclease A from bovine pancreas (R5125), α-chymotrypsinogen A Type II from bovine pancreas (C4879), and myoglobin from equine heart (M1882), Sigma product number indicated in parenthesis.

All purchased peptides and proteins were stored according to the manufacturer's recommendations and used as received to prepare solutions for injection by dissolution in water.

EXAMPLE 1

Synthesis of Capillaries Grafted With Zwitterionic Polymer Layer

A 130 cm length (for two capillaries) of the UV-transparent fused silica capillary was flushed with (in sequence) 0.1 M sodium hydroxide for 20 min, 0.1 M hydrochloric acid for 20 min, and finally with water for 20 min at room temperature. The inner wall of the capillary was then activated for grafting polymerization by attaching methacrylic anchoring groups. This was accomplished by filling the capillary with a 30% (v/v) solution of MAPTMS in acetone and allowing the reaction to take place for 18 hours at room temperature, with both ends of the tube sealed with pieces of rubber cut from a silicon rubber stopper. This treated capillary was then washed with acetone for 15 minutes followed by washing with water for 15 minutes. All flushing of reagents and washing solutions was accomplished by nitrogen overpressure at 600 kPa.

A graft polymerization solution containing 8 mg of BME photo-initiator, 400 mg of SPE, 2 mL methanol, and 2 mL of water was prepared and degassed with helium for 15 minutes. The activated capillary was then filled with this solution and sealed at both ends with a piece of silicon rubber, whereafter the photograft polymerization took place for 30 minutes using a Spectrolinker XL 1500 UV crosslinker (Spectronics Corp. Westbury, N.Y.) as the light source. This unit was equipped with eight 15 W fluorescent black tubes (F15T8/BLB; GTE Sylvania), producing UV light of predominantly 365 nm wavelength. After polymerization, the capillary was flushed for 30 minutes from each end with 0.1 M NaCl, followed by water for 10 minutes. The capillary was fixed in the cartridge and preconditioned with 35 mM phosphate buffer, pH 7 by applying first 25 kV then –25 kV, one hour each.

Accordingly, a two-step scheme was chosen to synthesize the capillary by grafting a zwitterionic polymer layer on the inner surface. As mentioned above, the silanol groups on the native capillary were first reacted with 3-methacryloyloxypropyl-trimethoxysilane, which produces methacrylic anchors on the surface covalently bonded through a Si—O—Si—C linkage (Li et al, J. Anal. Biochem. 1994, 223, 153-158). When the capillary was filled with the polymerization solution containing SPE monomer and photoinitiator, the polymerization was started by 365 nm UV light. The transparent capillary was used because the photo-polymerization approach was applied, which is a faster free radical polymerization compared with thermal polymerization. During the polymerization step, the surface-attached methacrylic groups are incorporated in the growing polymer chains through a "grafting through" procedure, in which the same polymer chain can incorporate several surface methacrylic groups leading to multi-point attachment. A schematic illustration in Scheme 1 shows this two-step reaction used to obtain the zwitterionic polymeric graft on the capillary inner surface. A 100 mM NaCl solution was used to flush the capillary clean after the grafting polymerization, in order to remove the unreacted or unattached monomer and polymer. The use of salt is necessary because of the "anti-polyelectrolytic" solubility behavior of zwitterionic polymers, i.e., their solubility increases with increasing ionic strength.

EXAMPLE 2

EOF Measurements

EOF measurements were made by hydrodynamic injection of 5 mM benzyl alcohol at 0.5 psi for 4 seconds and energizing the CE system with 25 kV (cathode at outlet). Four replicates were taken for each buffer solution. An untreated capillary was used as "blank" and was preconditioned with 0.1 M NaOH for 5 minutes, with water for 5 minutes, and 3 minutes with 25 mM sodium phosphate buffer, pH 7. This procedure was used only for the native capillary, not for the MAPTMS-activated and SPE-grafted capillaries, since treatment with NaOH could result in hydrolytic cleavage of the covalently-attached modified layers from the silica surface. Prior to the introduction of each new sample or separation buffer, all capillaries were rinsed for 3 minutes with 100 mM stock buffer solution with the same pH as the actual separation buffer, then for 2 minutes with water, and 3 minutes with the separation buffer; all solutions were driven by a "high pressure" set by the instrument (20 psi). A two minute pre-rinsing with separation buffer was applied before each separation. The EOF mobility was determined according to the following formula:

$$\mu_{EOF} = L_d L_t / t_m V \quad [1]$$

Where $L_d$ is the effective capillary length (from the injection end to the detector), $L_t$ is the total capillary length, $t_m$ is the migration time of a neutral marker, and V is the applied electric field.

Hence, the capillaries were tested for their EOF properties in all stages of the preparation: the native capillary, after MAPTMS activation, and the final SPE-grafted capillary. The reason the EOF was measured for the MAPTMS-activated capillary is because it was desirable to see if the EOF suppression was due to reduction of surface silanol groups from the activation step or from the grafting polymerization of the zwitterionic monomer SPE. In Table 1, the $\mu_{EOF}$ calculated from the migration times of the neutral marker and the migration times for $Br^-$, $NO_3^-$ and $SCN^-$ ions on these three capillaries are summarized, using 25 mM phosphate buffer, pH 7, as separation buffer and benzyl alcohol as neutral marker. It can be seen that the difference between $\mu_{EOF}$ of the native and the MAPTMS activated capillaries was very small; however, there was a profound decrease in EOF on the SPE-grafted capillary. The EOF was suppressed by more than five times, compared with the native and MAPTMS-activated capillaries. This demonstrates the grafted zwitterionic polymer layer has a strong effect on the suppression of EOF.

While not intending to be bound by theory, considering the two step chemistry used in the modification of the capillaries there may be two reasons for this strong EOF suppression. The surface charge density may be reduced by the large fraction of silanol groups that are reacted in the MAPTMS activation procedure, intended to form covalent links between the zwitterionic polymer layer and the capillary wall. The observed decrease in EOF as a result of the MAPTMS activation procedure was only from 6.72 to 5.98 m²/Vs, showing that the activation procedure had only a limited effect on the EOF. Therefore, the large decrease in EOF to 1.11 m²/Vs in the SPE grafted capillary is more likely due to shielding or dissipation of the residual silanol group charges by the zwitterionic polymer layer.

Three inorganic anions were also used as test probes to determine the extent of EOF suppression on these three different capillaries. The migration times for these three anions on SPE-grafted capillary were less than 3 minutes; see Table 1. Thiocyanate ion could not be detected within 30 minutes on the native capillary because of slower electrophoretic mobility. On the other hand, it was also seen from the electropherograms that the efficiencies and peak shapes were much better with the SPE-grafted capillary, i.e., the peaks had characteristic tailing and extremely long migration times on both the native and the MAPTMS-activated capillaries (not shown).

TABLE 1

Comparison of electroosmotic flow ($\mu_{EOF}$) and migration time for neutral marker and three inorganic anions on three different capillaries.

| Capillary | $\mu_{EOF}$ (m²/Vs) | Benzyl alcohol (min) | Br⁻ (min) | NO₃⁻ (min) | SCN⁻ (min) |
|---|---|---|---|---|---|
| Blank | 6.72 | 2.83 | 8.35 | 15.51 | >30[a] |
| MAPTMS | 5.98 | 3.18 | 6.64 | 9.66 | 11.83 |
| SPE | 1.11 | 17.11 | 2.44 | 2.76 | 2.96 |

[a]No peak detected in 30 minutes.

EXAMPLE 3

Separation of Inorganic Anions

A new modified capillary (50 cm to detector, 57 cm in total) was used for the separation of a mixture containing 1 mM each of bromide, nitrite, nitrate, thiocyanate, molybdate, tungnate, bromate, and iodate ions (as sodium or potassium salts), as well as for their individual solutes (1 mM of each ion). When a new separation buffer or a new type of sample was changed, the capillary was rinsed by the same rinse procedure as above. Two minutes pre-rinsing was also done with the separation buffer before each separation. The mixtures of anions were injected using low pressure-driven hydrodynamic injection at 0.5 psi for 4.0 seconds. The applied potential was −25 kV (anode at outlet) and a detector rise time of 1.0 second was used. The number of theoretical plates determined the separation efficiency, according to:

$$N=5.54(t_m/w_{1/2})^2 \quad [2]$$

Where N is the number of theoretical plates for the capillary, $t_m$ represents the migration time of a neutral marker, and $w_{1/2}$ is the peak width at half the peak height.

The optimal separation conditions for a mixture of inorganic anions, which contained 1 mM each of Br⁻, NO²⁻, NO₃⁻, SCN⁻, MoO₄²⁻, BrO₃⁻, WO₄²⁻ and IO₃⁻ in water, were thus studied on SPE-grafted capillaries using phosphate buffer at three different concentrations, each concentration provided at three different pH values. The effects of buffer concentration and pH on EOF and migration times of the neutral marker and inorganic anions are summarized in Table 2 and 3. A typical electropherogram is shown in FIG. 1, where all eight anions tested were well separated in five minutes.

As seen in Table 2, the EOF decreased with increasing buffer concentration. When plotting the data for $\mu_{EOF}$ against the 1/$\sqrt{C}$ from the experiment at pH 7 in Table 2, it is apparent that there is a linear relation ($R^2$=0.983) and the profiles are similar to those described in Atamna, I. Z.; Issaq, H. J.; Muschik, G. M.; Janini, G. M. *J. Chromatogr.* 1991, 588, 315-320, except the migration times were replaced with calculated $\mu_{EOF}$. This could be due to compression of the double layer by the increased buffer concentration, and thus a decreased $\zeta$-potential with a correspondingly reduced EOF. It is well known that the EOF of a native capillary is determined by the degree of dissociation of the silanol groups and the ionic strength of the separation buffer. A higher pH value means a higher the degree of dissociation, leading to a higher EOF. However, the capillary with grafted zwitterionic polymer layer showed an opposite behavior, where the EOF appeared to decrease with increasing pH. This was attributed as an effect from the changes in separation buffer ionic composition as the pH changed, because although the nominal concentration was 25 mM for the phosphate buffers of pH 6, 7 and 8, the $H_2PO_4^-$ to $HPO_4^{2-}$ ratios and sodium ion concentrations differed from each other. This is evident not least from the increasing current from 24.2 to 39.0 and 49.5 µA at −25 kV, when the pH changed from 6 to 7 and 8.

TABLE 2

Effect of buffer pH and concentration on $\mu_{EOF}$ with SPE grafted capillary.

| EOF | pH 6 | | | pH 7 | | | pH 8 | | |
|---|---|---|---|---|---|---|---|---|---|
| | 25 mM | 35 mM | 45 mM | 25 mM | 35 mM | 45 mM | 25 mM | 35 mM | 45 |
| $\mu_{EOF}$ (m²/Vs) | 1.24 | 1.05 | 0.98 | 1.11 | 1.01 | 0.97 | 1.08 | 0.94 | 0.83 |
| BA[a] (min) | 15.36 | 18.18 | 19.47 | 17.11 | 18.88 | 19.59 | 17.63 | 20.28 | 22.97 |

[a]Appearance time for the neutral marker benzyl alcohol.

In Table 3, it can be seen that the migration times for all tested anions decreased with increasing buffer concentration from 25 to 35 and 45 mM at all three pH levels tested. This could be the effect of the concomitant reduction of EOF, which shortened the migration times due to the counter EOF mode. The separation efficiency for the tested anions has also been calculated; BrO₃⁻ showed the highest efficiency of 333,000 plates/m using 25 mM phosphate buffer, pH 8.

TABLE 3

Effect of buffer pH and concentration on the migration times of inorganic anion separations with SPE-grafted capillaries.

| Anion | pH 6 | | | pH 7 | | | PH 8 | | |
|---|---|---|---|---|---|---|---|---|---|
| | 25 mM | 35 mM | 45 mM | 25 mM | 35 mM | 45 mM | 25 mM | 35 mM | 45 mM |
| Br⁻ | 2.65 | 2.50 | 2.40 | 2.44 | 2.28 | 2.15 | 2.36 | 2.18 | 2.00 |
| NO₂⁻ | 2.89 | 2.72 | 2.61 | 2.66 | 2.48 | 2.33 | 2.56 | 2.36 | 2.16 |
| NO₃⁻ | 2.99 | 2.82 | 2.70 | 2.76 | 2.58 | 2.43 | 2.66 | 2.46 | 2.26 |
| SCN⁻ | 3.24 | 3.02 | 2.88 | 2.96 | 2.74 | 2.56 | 2.84 | 2.60 | 2.37 |
| MoO₄²⁻ | 3.31 | 3.12 | 3.00 | 3.01 | 2.82 | 2.64 | 2.90 | 2.67 | 2.43 |
| WO₄²⁻ | 3.44 | 3.24 | 3.11 | 3.14 | 2.93 | 2.75 | 3.02 | 2.78 | 2.52 |
| BrO₃⁻ | 3.98 | 3.71 | 3.54 | 3.63 | 3.37 | 3.14 | 3.49 | 3.19 | 2.89 |
| IO₃⁻ | 6.07 | 5.49 | 5.15 | 5.26 | 4.78 | 4.39 | 5.01 | 4.49 | 3.98 |

Figure 2:
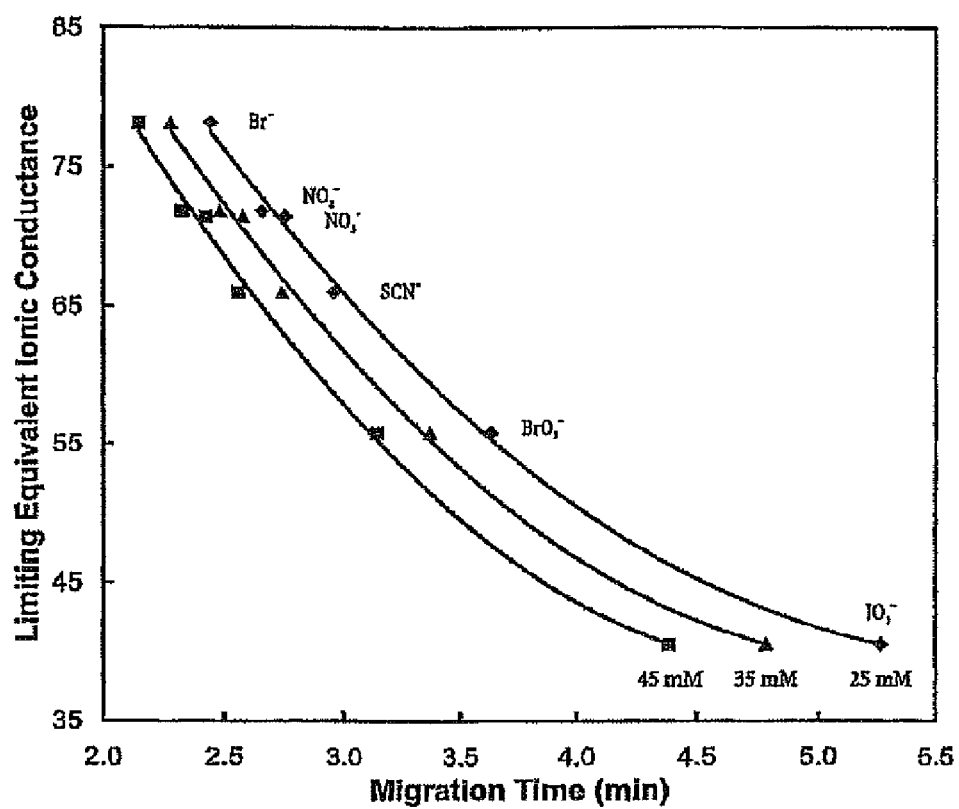
FIG. 2 shows a plot of Limiting Equivalent Ionic Conductance versus migration time of six inorganic anions at three concentration levels with pH 7.

To determine whether there was significant wall interactions involved in the separation, the limiting equivalent ionic conductance (LEIC) versus the migration time of each individual anion at three buffer concentration was plotted; see FIG. 2. The plots show the same tendency as described by Baryla et al, J. Chromatogr., A 2002, 956, 271-277, and Jones et al, Chromatogr. 1991, 546, 445-458. This implies that anions are separated according to their electrophoretic mobility in the electrolyte solution rather than by an interaction with the capillary wall "stationary phase," i.e., the separation was governed solely by their different electrophoretic mobility in the electrolyte solution when an electric field was applied through the open tubular capillary. The LEIC of the anions used as samples are as follows: $Br^-$ 78.1, $NO_2^-$ 71.8, $NO_3^-$ 71.4, $SCN^-$ 66, $BrO_3^-$ 0.55.8, $IO_3^-$ 40.5 (J. A. Dean (Ed.), Lange's Handbook of Chemistry, 13th Ed., McGraw Hill: New York, 1985, p 6-34). All data are in $S \cdot cm^2 \cdot equiv^{-1}$. $MoO_4^{2-}$ and $WO_4^{2-}$ are divalent anions and not included in FIG. 2.

Figure 3:
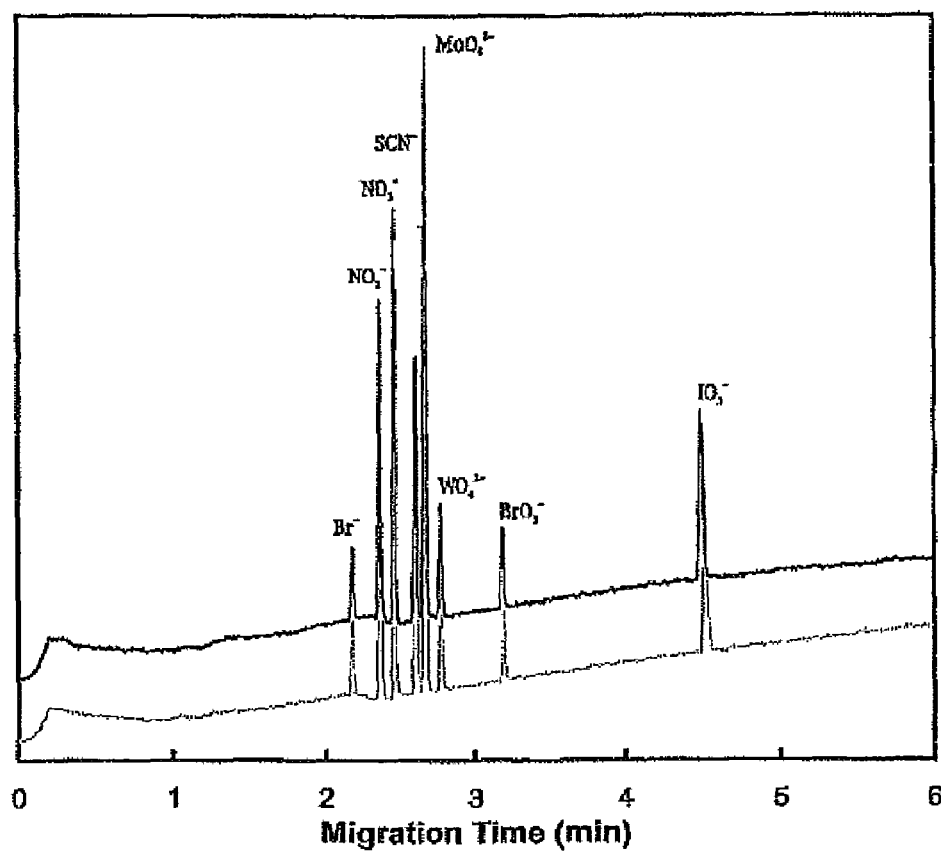
FIG. 3 relates to overlapping electropherograms showing the separation reproducibility of eight inorganic anions, where the black electropherogram represents the first injection for the capillary and the gray electropherogram is the separation after 100 injections, and where detection=214 NM, applied voltage=−25 kV, capillary=50 μm i.d. by 50/57 cm, separation buffer=35 mM pH 8 phosphate buffer.

To examine the stability of the capillary graft coated with the sulfobetaine-type zwitterionic polymer, 35 mM phosphate buffer, pH 8, was used as the separation buffer. This is the highest pH condition that was used due to the instability inherent in the silyl ether linkage used to attach the MAPTMS anchors. The same mixture of eight inorganic anions noted above was used in this procedure. FIG. 3 shows superimposed electropherograms from two separations, one immediately after the preparation of the grafted capillary, and the other after about 100 injections (15 minutes average running time for each injection), run under identical conditions. The largest drift in migration time was seen for iodate, for which the difference after 100 injections was less than 2 seconds, i.e., close to the range of experimental error. Therefore, the grafted zwitterionic polymer is stable under the optimal operating conditions.

Figure 4:
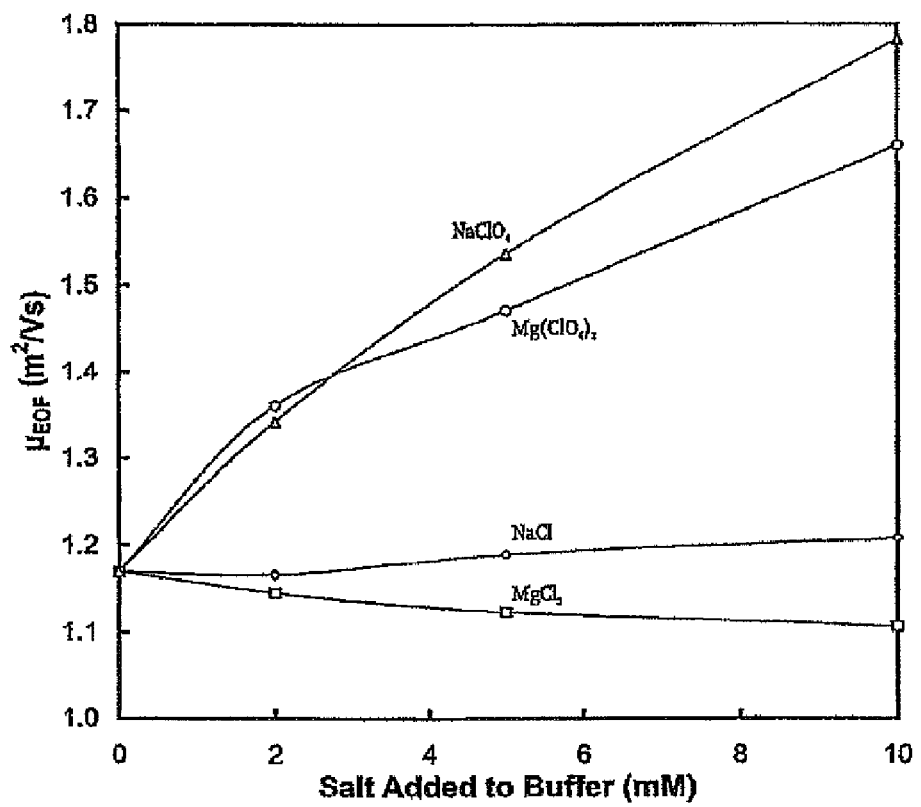
FIG. 4 presents the effect of various anions and cations on the electroosmotic flow, where the concentration on the abscissa is based on the concentration of anions added to 35 mM phosphate buffer, pH 7, and where the salts added were NaCl and NaClO$_4$ at 2, 5, and 10 mM, and MgCl$_2$ and Mg(ClO$_4$)$_2$ at 1, 2.5, and 5 mM.

Based on previous observations in liquid chromatographic systems (Jiang et al, Anal. Chem. 1999, 71, 333-344; Anal. Chem. 2001, 73, 1993-2003; Anal. Chem. 2002, 74, 4682-4687; Viklund et al, Macromolecules 2000, 33, 2539-2544; Viklund et al, Anal. Chem. 2001, 73, 444-452), it is assumed that the highly polarisable perchlorate ion is capable of entering into strong interactions with the quaternary ammonium layer, a process that will bind the positive charges and induce a net negative charge on the material surface. On the other hand, the sulfonic groups interact more strongly with divalent cations, which will reduce the negative charge on the surface of the zwitterionic polymer. FIG. 4 shows the effects of adding four different salts: NaCl, $NaClO_4$, $MgCl_2$ and $Mg(ClO_4)_2$, at different concentration levels to 35 mM phosphate buffer, pH 7. It is evident that the $\mu_{EOF}$ was fastest with $NaClO_4$ was added and slowest after the addition of $MgCl_2$. This is attributed to the ability of the perchlorate ion to form strong ion pairs with quaternary ammonium groups, thus inducing a stronger negative charge and a more negative ζ-potential. Because the EOF is a direct function of the ζ-potential, the EOF became faster compared to the measurement without added $NaClO_4$ salt, or with the addition of NaCl. When magnesium salts were added to the buffer solution, the divalent cation is expected to reduce the net negative charge on the capillary inner wall because of the preferred interaction of the sulfonic acid group in the zwitterionic polymer layer with polyvalent cations. Chloride ion seemed to interact with the zwitterionic groups in a manner similar to the phosphate ion. Comparing the $\mu_{EOF}$ with NaCl and $MgCl_2$ added to the separation buffer, there is a 10% difference at the separation buffer concentration of 35 mM buffer plus 10 mM salt. This is similar to the findings of Baryla et al., that the changes in $\mu_{EOF}$ following the addition of divalent ions is less than 10% on capillaries that have been dynamically modified with zwitterionic detergent (Baryla et al, Anal. Chem. 2000, 72, 2280-2284). It was also found in this work that perchlorate ion has a stronger effect on EOF than $Mg^{2+}$ when comparing the $\mu_{EOF}$ values obtained with $MgCl_2$, $Mg(ClO_4)_2$, NaCl and $NaClO_4$ added to the separation buffer.

EXAMPLE 4

Separation of Peptides and Proteins

A capillary with 40 cm to detector and 47 cm total length was chosen in the separation of peptides and proteins. The solute concentration used in the separations was 0.1 mg/mL for the small peptides and 0.2 mg/mL for the proteins, both for the mixtures and individual solute samples. The rinse procedure was the same as the one in the EOF measurements. A 2 minute pre-rinsing with separation buffer was also included before each separation. The small peptide mixture and individual samples were injected using low pressure-driven hydrodynamic injection at 0.5 psi for 4.0 seconds. The protein samples were injected for 15 seconds by the same procedure. The applied potential during the separations was 20 kV for the small peptides and 15 kV for the proteins (cathode at outlet). Equation 2 was also used to calculate the number of theoretical plates, which determines the separation efficiency for proteins and peptides.

Figure 5:
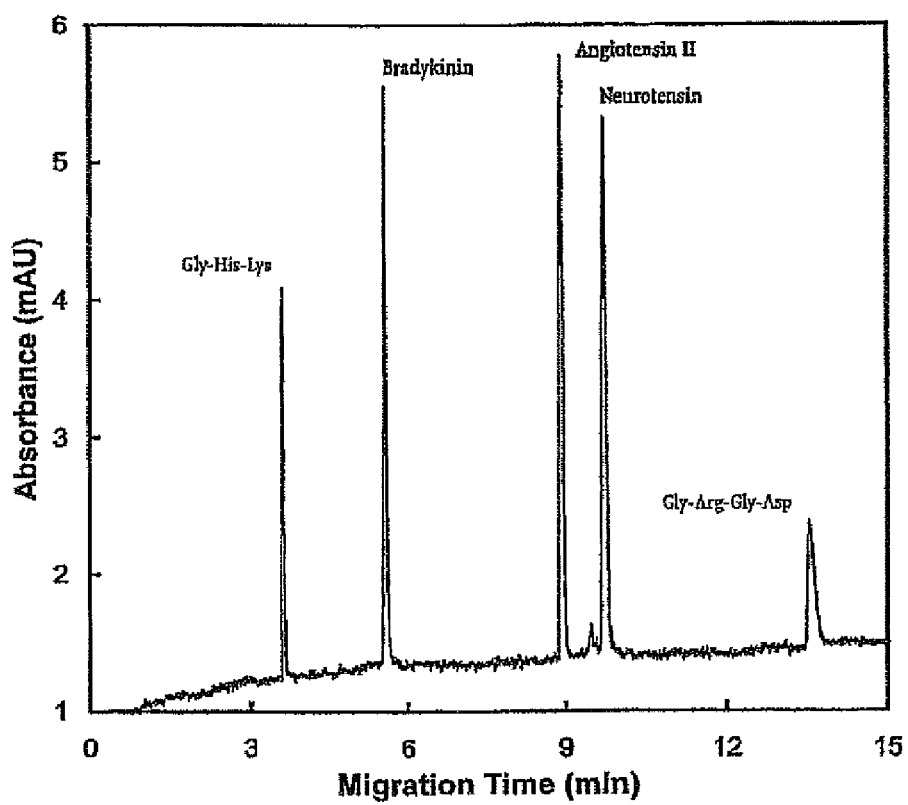
FIG. 5 shows separation of five common peptides: Gly-His-Lys, bradykinin, angiotensin II, neurotensin and Gly-Arg-Gly-Asp, where detection =214 nm, applied voltage =20 kV, capillary =50 μm i.d. by 40/47 cm, separation buffer=40 mM ammonium acetate buffer at pH 5.

The continued investigations on this SPE grafted capillary were hence focused on the separation of biomolecules such as small peptides and proteins. Peptide separation on native silica capillaries is problematic due to wall adsorption and high EOF, which result in very fast migration with the co-EOF mode and poorer separation. In order to get a reasonable separation on a non-modified capillary, very high buffer concentration needs to be used to suppress the EOF. As shown above, the EOF of the SPE-grafted capillary was strongly suppressed by the zwitterionic polymer layer. It would therefore be useful for small peptide separations under very mild separation conditions. FIG. 5 shows the separation of a mixture containing five peptides: Gly-His-Lys, Bradykinin, Angiotensin II, Neurotensin, and Gly-Arg-Gly-Asp, using 40 mM ammonium acetate buffer, pH 5. Separation buffers with other pH and concentrations were also studied, 40 mM was found to be a sufficiently high concentration of ammonium acetate to produce a good separation of the peptide mixture with very good peak shape and efficiency. The migration times and efficiencies for all tested peptides are summarized in Table 4.

Figure 6:
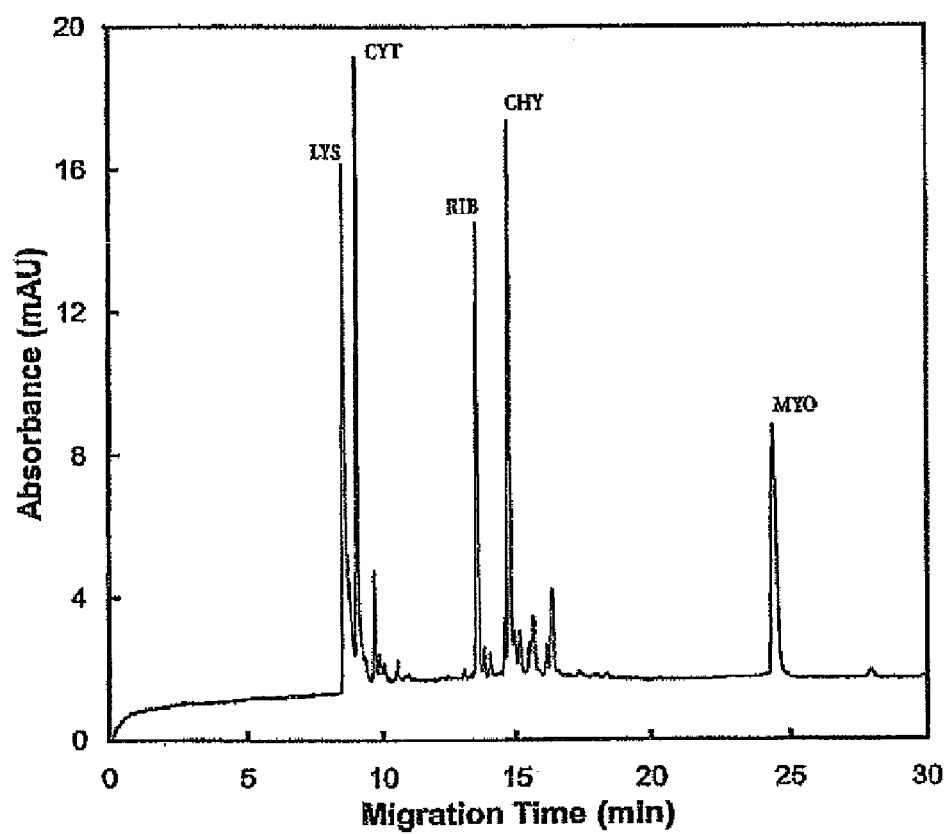
FIG. 6 discloses an electropherogram from the separation of five basic proteins: lysozyme (LYS), cytochrome C (CYT), α-chymotrypsinogen A (CHY), ribonuclease (RIB) and myoglobin (MYO), where detection =214 nm, applied voltage =15 kV, capillary =50 μm i.d. by 40/47 cm, injection =hydrodynamic injection for 15 seconds, separation buffer=40 mM pH 7 ammonium acetate buffer with 15 mM MgCl$_2$.

When it was surprisingly realized that the zwitterionically-grafted capillary could be used for the separation of small peptides at high efficiency, the separation of a mixture containing five basic proteins was attempted. The first separation parameters to be evaluated were buffer concentration and pH. However, even though a buffer concentration higher than 100 mM was used, it was not possible to get a good resolution of this protein mixture with an acceptable peak shape. The grafted sulfobetaine type of zwitterionic capillary may show a cation exchange property, as observed in a previous study (Anal. Chem. 2002, 74, 4682-4687; Viklund et al, Macromolecules 2000, 33, 2539-2544; Viklund et al, Anal. Chem. 2001, 73, 444-452), because of the spatial arrangement of the quaternary ammonium groups and sulfonic groups on the zwitterionic moieties. However, the ζ-potential will be less negative if magnesium ions are added in the solution, owing to the interaction with sulfonic groups and the induction of less negative charge (see the EOF studies above) (Chen et al, Anal. Chem. 1993, 65, 2770-2775; Pietryk et al, Chromatogr., A 1997, 775, 327-338; Minnoor et al, J. Chromatogr., A 2000, 884, 297-309). When 15 mM of $MgCl_2$ was added to the 40 mM ammonium acetate buffer, pH 7, the five basic proteins were well separated with good efficiency; see FIG. 6. The retention times and efficiencies for different proteins are listed in Table 4.

TABLE 4

Migration time ($t_m$) and separation efficiency of peptides and proteins separated with the SPE grafted capillary.

| Peptide/protein | pI[a] | $t_m$ min | Efficiency N/m |
|---|---|---|---|
| Gly-His-Lys | 10.1 | 3.61 | 113,000 |
| Bradykinin | 12.4 | 5.54 | 135,000 |
| Angiotensin II | 7.8 | 8.90 | 216,000 |
| Neurotensin | 10.0 | 9.70 | 176,000 |
| Gly-Arg-Gly-Asp | 6.8 | 13.52 | 309,000 |
| Lysozyme | 11.0 | 8.15 | 109,000 |
| Cytochrome C | 10.2 | 8.67 | 221,000 |
| α-Chymotrypsinogen A | 9.2 | 13.16 | 435,000 |
| Ribonuclease | 9.3 | 14.36 | 398,000 |
| Myoglobin | 7.3 | 24.33 | 163,000 |

[a]The pI values of the proteins (below the dividing line) are from Towns wt al, Anal. Chem. 1991, 63, 1126-1132, whereas the peptide pI's are calculated using the pI function of L'Atelier BioInformatique de Marseille (A.B.I.M., http://www.up.univ-mrs.fr/~wabim/).

The buffers with pH 6 and 8 were also tested on the SPE grafted capillary in order to find an even better separation condition for this protein mixture, especially in order to improve the resolution between the lysozyme and cytochrome C. It was found that the migration time for all five tested proteins decreased at pH 6, because the net charges of the proteins increase due to the protonation, which in turn increases the electrophoretic mobility of proteins. However, the separation resolution between lysozyme and cytochrome C became worse. When pH 8 buffer was used, myoglobin could not be seen within 30 minutes because of the low charge. Consequently, pH 7 was chosen as an optimum because it provided the highest resolution between lysozyme and cytochrome C, and a reasonable migration time for myoglobin.

EXAMPLE 5

Synthesis of Zwitterionic Capillaries by Thermo-Initiated Graft Polymerization

A 180 cm long piece of the polyimide-coated fused silica capillary of the previous examples (sufficient for three capillaries) was flushed with (in sequence) 0.1 M sodium hydroxide for 20 minutes, 0.1 M hydrochloric acid for 20 minutes, and finally with water for 20 minutes at room temperature. Methacrylic anchoring groups were attached to the inner wall of the capillary by filling with a 30% (v/v) solution of MAPTMS in acetone and allowing the reaction to proceed for 18 hours at room temperature, with both ends of the tube sealed by silicone rubber cut from a stopper. This treated capillary was then washed with acetone for 15 minutes. All flushing of reagents and washing solutions was accomplished by nitrogen overpressure at 600 kPa.

A graft polymerization solution containing 8 mg of 2,2'-azobis{2-methyl-N-[2-(1-hydroxybutyl)propionamide} (V-085) (obtainable from Wako Chemical, Osaka, JP), 400 mg N,N-dimethyl-N-methacryloxyethyl-N-(3-sulfopropyl) ammonium betaine (SPE) and 4 ml water was prepared and degassed with helium for 15 minutes. The activated capillary was filled with this solution and sealed at both ends by a piece of silicon rubber; thereafter, the thermo-initiated graft polymerization took place for 3 hours at 85° C. by submersion into a water bath. After polymerization, the capillary was flushed for 30 minutes with 0.1 M NaCl, followed by water for 10 minutes. The capillary was fixed in the cartridge and preconditioned with 35 mM phosphate buffer, pH 7, by applying first 25 kV for 1 hour and then –25 kV for 1 hour.

Figure 7:
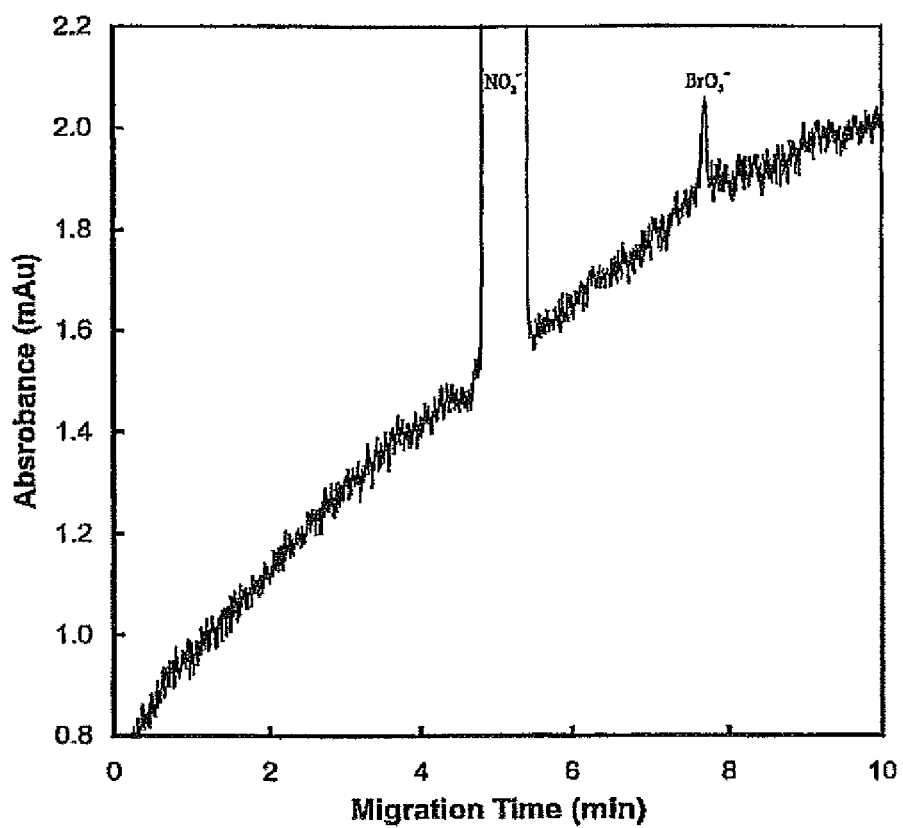
FIG. 7 presents an electropherogram for the detection of low concentration of bromate ion (10 μM bromate in 1 mM each of chloride and nitrate), where detection=214 nm, applied voltage=−20 kV, capillary=75 μm i. d. by 50/57 cm, separation buffer=10 mM pH 7 phosphate buffer, injection=electrokinetic injection for 15 seconds at −6 kV.

The capillary (50 cm to detector and 57 cm in total) was used for detecting a low concentration of bromate ion (10 μM) in a solution of 1 mM chloride and 1 mM nitrate as sodium or potassium salts. The bromate ion is a carcinogenic compound present in potable water. Prior to the introduction of a new sample or separation buffer, the capillary was rinsed for 3 minutes with 100 mM stock buffer solution with the same pH as the actual separation buffer, then for 2 minutes with water, and 3 minutes with the separation buffer; all solutions driven by the "high pressure" set by the instrument (20 psi). A two minute pre-rinsing with separation buffer was applied before each separation. The bromate was well separated from two common interfering ions, nitrate and chloride, both at 100 times higher concentration in the sample solution. The electropherogram is shown in FIG. 7.

Figure 8:
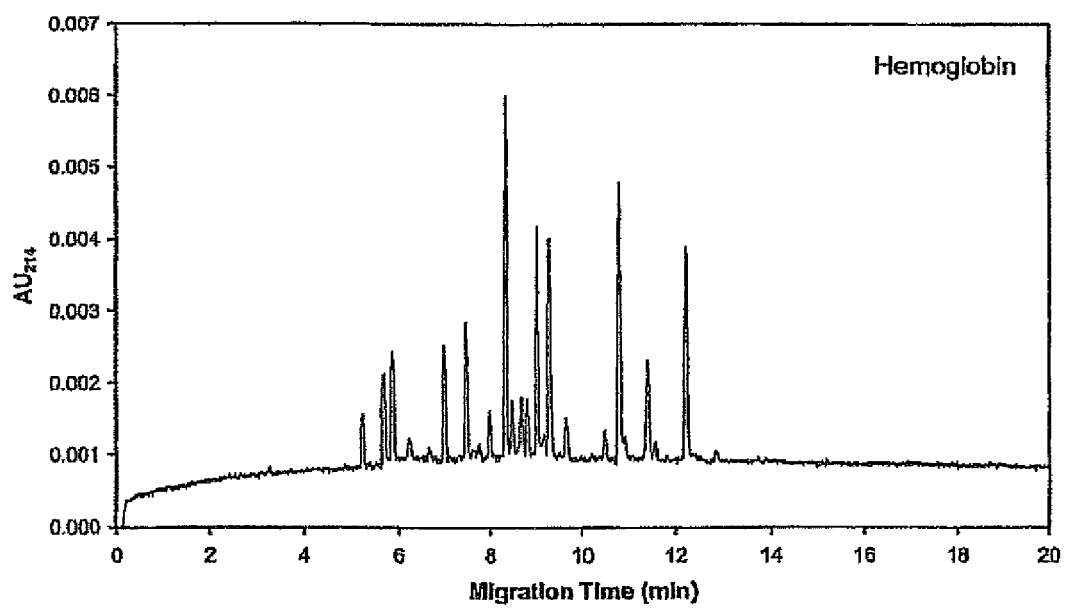
FIG. 8 shows an electropherogram from separations of typically digested hemoglobin where detection=214 nm, applied voltage=20 kV, capillary=50 μm i. d. by 50/57 cm, injection=electrokinetic injection for 10 seconds at 10 kV, separation buffer=40 mM pH 2.5 phosphate buffer with 15 mM MgCl$_2$.
Figure 9:
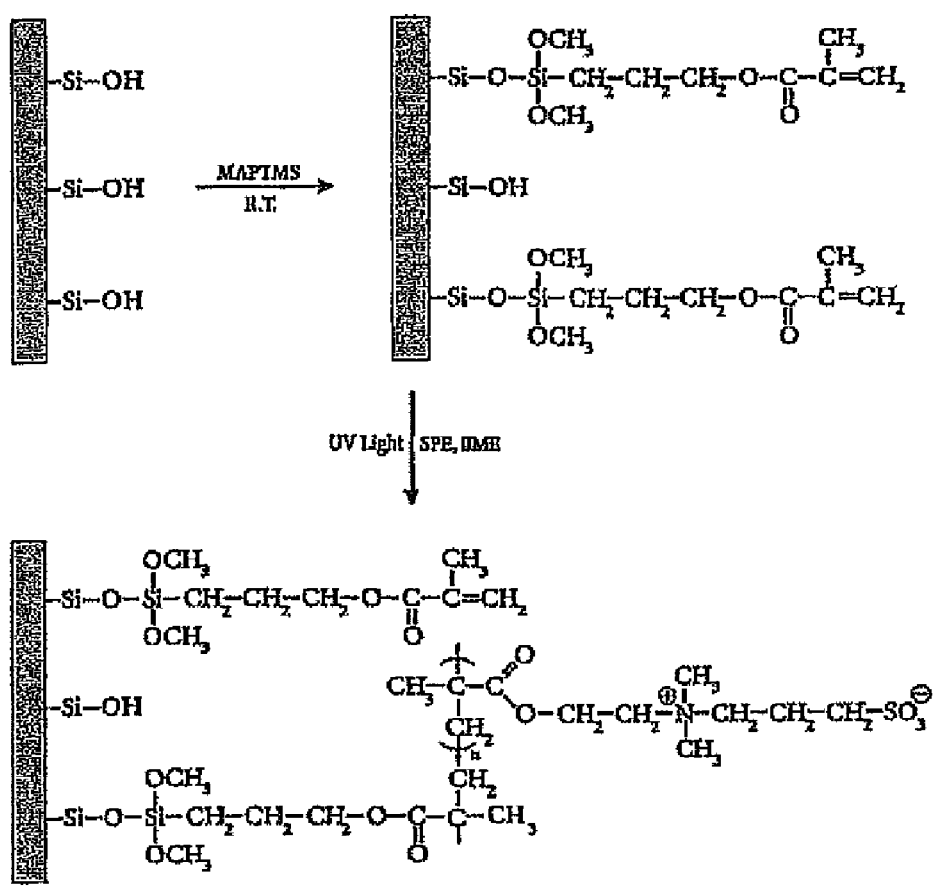
FIG. 9 depicts Scheme 1, which shows the reaction scheme for the synthesis of the CE capillary grafted with SPE zwitterionic polymeric layer.
Figure 10:
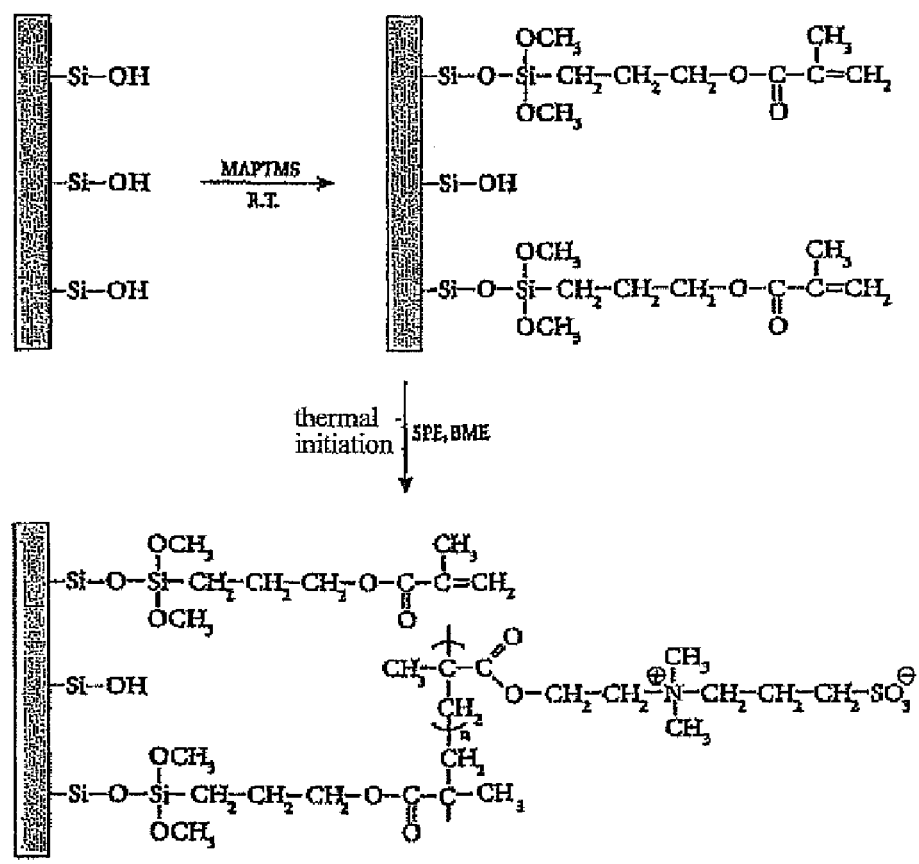
FIG. 10 depicts Scheme 2, which discloses a reaction scheme for the synthesis of the CE capillary grafted with SPE zwitterionic polymeric layer via thermally initiated polymerization.

The capillary was also used for separating tryptically digested proteins. Phosphate buffer (40 mM, pH 2.5) with the addition of 15 mM $MgCl_2$ was used as separation buffer. The digested protein sample were prepared by adding 0.2 ml Milli-Q water in original sample tubes which contained digest corresponding to 500 pmole of each protein before digestion. The final concentration corresponded to 2.5 μM protein. The rinse procedure was the same as outlined above. The test samples were injected using electrokinetic injection at 10 kV for 10 seconds. The applied potential during the separations was 20 kV. FIG. 8 shows an electropherogram of low molecular weight digests of hemoglobin.

We claim:

1. An open tube for use in electrophoretic or chromatographic separation of materials, comprising:
   a tube of fused silica,
   wherein said tube has an interior surface; and
   wherein said interior surface comprises covalently bound zwitterionic betaine groups.

2. An open tube according to claim 1, wherein said tube is a capillary tube.

3. An open tube according to claim 2, wherein said zwitterionic betaine groups have the following structure:

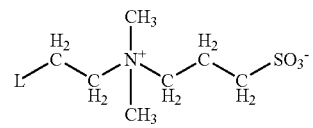

wherein L is a linking group.

4. An open tube according to claim 2, wherein said zwitterionic betaine groups are selected from the group consisting of
   a) methacrylic acid amidopropyl-dimethyl ammonium betaine,
   b) N,N-dimethyl-N-methacryloxyethy-1-N-(3 -sulfopropyl)-ammonium betaine,
   c) pyridinium, 2-ethenyl-1-(3-sulfopropyl)-hydroxide, inner salt, and
   d) trimethoxysilylpropyl-N-(3-sulfopropyl)-ammonium betaine.

5. An open tube according to claim 2, wherein said capillary tube is UV-transparent.

* * * * *

UNITED STATES PATENT AND TRADEMARK OFFICE
CERTIFICATE OF CORRECTION

PATENT NO. : 7,632,389 B2  Page 1 of 1
APPLICATION NO. : 10/819215
DATED : December 15, 2009
INVENTOR(S) : Wen Jiang et al.

It is certified that error appears in the above-identified patent and that said Letters Patent is hereby corrected as shown below:

Title page (75) Inventors reads:" Inventors: Jiang Wen, Umea (SE); Knut Irgum, Bullmark (SE)" Should read: --Inventors: Wen Jiang, Umea (SE); Knut Irgum, Bullmark (SE)--

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,632,389 B2 Page 1 of 1
APPLICATION NO. : 10/819215
DATED : December 15, 2009
INVENTOR(S) : Wen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1602 days.

Signed and Sealed this

Twenty-first Day of December, 2010

David J. Kappos
*Director of the United States Patent and Trademark Office*